(12) United States Patent
Chen et al.

(10) Patent No.: US 12,213,732 B2
(45) Date of Patent: Feb. 4, 2025

(54) ASSESSING VISUAL FUNCTION

(71) Applicant: The Schepens Eye Research Institute, Inc., Boston, MA (US)

(72) Inventors: Dong Feng Chen, Newtonville, MA (US); Gang Luo, Lexington, MA (US); Cong Shi, Boston, MA (US); Kin-Sang Cho, Winchester, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 1078 days.

(21) Appl. No.: 17/044,606

(22) PCT Filed: Apr. 3, 2019

(86) PCT No.: PCT/US2019/025618
§ 371 (c)(1),
(2) Date: Oct. 1, 2020

(87) PCT Pub. No.: WO2019/195450
PCT Pub. Date: Oct. 10, 2019

(65) Prior Publication Data
US 2021/0068650 A1 Mar. 11, 2021

Related U.S. Application Data

(60) Provisional application No. 62/652,282, filed on Apr. 3, 2018.

(51) Int. Cl.
*A61B 3/00* (2006.01)
*A61B 3/11* (2006.01)
(Continued)

(52) U.S. Cl.
CPC .......... *A61B 3/0091* (2013.01); *A61B 3/0025* (2013.01); *A61B 3/0041* (2013.01);
(Continued)

(58) Field of Classification Search
CPC ... A61B 3/0091; A61B 3/0025; A61B 3/0041; A61B 3/112; A61B 3/113; A61B 3/14;
(Continued)

(56) References Cited

U.S. PATENT DOCUMENTS

2010/0283969 A1* 11/2010 Cooperstock .......... A61B 3/022
351/201
2012/0276127 A1 11/2012 Adamus et al.
(Continued)

OTHER PUBLICATIONS

Kretschmer et al. "A system to measure the Optokinetic and Optomotor response in mice", Journal of neuroscience methods. Dec. 30, 2015, 256:91-105.
(Continued)

*Primary Examiner* — Alex M Valvis
*Assistant Examiner* — Nidhi N Patel
(74) *Attorney, Agent, or Firm* — Fish & Richardson P.C.

(57) ABSTRACT

Methods, systems, and devices are provided for assessing visual function, especially in animals. For example, a device can be used for assessing visual functions, such as PLR and OMR, in animals that includes a visual stimulus unit. The device can also include one or more input devices that include at least one camera that is configured to monitor movement of the test subject and a processor that is configured to analyze the movement of the test subject taken by the camera and to assess visual functions of the test subject. The device can be used in a system including a designated general location for the test subject in which the test subject can see the visual stimulus unit and move freely while being monitored by the camera.

20 Claims, 11 Drawing Sheets

(51) Int. Cl.
  *A61B 3/113* (2006.01)
  *A61B 3/14* (2006.01)
  *A61B 5/00* (2006.01)
  *A61B 5/11* (2006.01)

(52) U.S. Cl.
  CPC .............. *A61B 3/112* (2013.01); *A61B 3/113* (2013.01); *A61B 3/14* (2013.01); *A61B 5/0075* (2013.01); *A61B 5/1114* (2013.01); *A61B 2503/40* (2013.01); *A61B 2503/42* (2013.01)

(58) Field of Classification Search
  CPC ..... A61B 3/032; A61B 3/0033; A61B 5/0075; A61B 5/1114; A61B 2503/40; A61B 2503/42
  See application file for complete search history.

(56) References Cited

U.S. PATENT DOCUMENTS

2013/0176534 A1   7/2013   Frankfort et al.
2014/0320817 A1   10/2014  Kiderman et al.
2016/0000871 A1   1/2016   Quaggin

OTHER PUBLICATIONS

Goller et al. "Hummingbirds control hovering flight by stabilizing visual motion", PNAS, Dec. 23, 2014; 111(51): 18375?18380.
Abdeljalil et al., "The optomotor response: A robust first-line visual screening method for mice", Vision research. Jun. 4, 2004 (Jun. 4, 2004), 45(11):1439-46.
Kretschmer et al., "OMR-Arena: Automated Measurement and Stimulation System to Determine Mouse Visual Thresholds Based on Optomotor Responses", PLOS One, Nov. 15, 2013.
Written Opinion of the International Searching Authority for International Patent Application No. PCT/US2019/025618 mailed Jul. 5, 2019 (8 pages).
International Search Report for International Patent Application No. PCT/US2019/025618 mailed Jul. 5, 2019 (2 pages).
PCT Preliminary Report on Patentability in International Appln. No. PCT/US2019/025618, dated Oct. 15, 2020, 10 pages.
Prusky et al., "Rapid Quantification of Adult and Developing Mouse Spatial Vision Using a Virtual Optomotor System," Invest. Opthalmol. Vis. Sci., 2004, 45(12):4611-4616.
Shi et al., "Optimization of Optomotor Response-based Visual Function Assessment in Mice," Sci Rep., 2018, 8:9708, 10 pages.

* cited by examiner

FIG. 12

| No. | Work | Method | Subjects | CS | VA (cpd) | Peak freq. (cpd) |
|---|---|---|---|---|---|---|
| 1 | Gianfranceschi et al. | Operant | 4 WT (C57BL/6J) | - | 0.5 | 0.15 |
| 2 | Prusky et al. | Operant | 5 WT (C57BL/6) | 6 | 0.55 | 0.2 |
| 3 | Busse et al. | Operant | 7 WT (C57BL/6J) + 5 trans (2 HHrtTAXK and 3 TRE/ASTBDN-1) | 5 ~ 10 | - | 0.13 |
| 4 | Histed et al. | Operant | 3 WT (C57BL/6-Balb/c hybrid) | 50 | 0.6 | 0.05 ~ 0.1 |
| 5 | Sinex et al. | OKR | 6 WT (C57BL/6J) | - | 0.5 | 0.125 |
| 6 | Tabata et al. | OKR | 14 WT (C57BL/6J) | 7 | 0.5 | 0.125 |
| 7 | Benkner et al. | OKR | 12 WT (C57BL/6) | 12.5 | 0.4 | 0.15 |
| | | | 4 $rd10$ @6wk | 5 | 0.35 | 0.15 |
| 8 | van Alphen et al. | OKR | 15 WT (C57BL/6) | 100 | 0.5 | 0.17 |
| 9 | Kretschmer et al. | OKR | 10 WT (C57BL/6J) | 20 | 0.4 | 0.15 ~ 0.2 |
| | | OMR | 7 WT (C57BL/6J) | | | |
| 10 | Kretschmer et al. | OMR | 6 WT (C57BL/6J) | - | 0.4 | 0.2 |
| 11 | Prusky et al. | OMR | 11 WT (C57BL/6) | 24.5 | - | 0.064 |
| | | | 17 WT (C57BL/6) | - | 0.4 | - |
| 12 | Abdeljalil et al. | OMR | 10 WT (C57BL/6J) | - | 0.52 | 0.26 |
| 13 | Ours | OMR | 10 WT (C57BL/6J) | 25 | 0.53 | 0.19 |
| | | | 11 $Rho^{-/-}$@6wk | 35 | 0.56 | - |

| | |
|---|---|
| 1. | Gianfranceschi, L., Fiorentini, A. & Maffei, L. Behavioural visual acuity of wild type and bcl2 transgenic mouse. *Vision research* 39, 569-574 (1999). |
| 2. | Prusky, G. & Douglas, R. Characterization of mouse cortical spatial vision. *Vision research* 44, 3411-3418 (2004). |
| 3. | Busse, L. et al. The detection of visual contrast in the behaving mouse. *Journal of Neuroscience* 31, 11351-11361 (2011). |
| 4. | Histed, M. H., Carvalho, L. A. & Maunsell, J. H. Psychophysical measurement of contrast sensitivity in the behaving mouse. *Journal of neurophysiology* 107, 758-765 (2012). |
| 5. | Sinex, D. G., Burdette, L. J. & Pearlman, A. L. A psychophysical investigation of spatial vision in the normal and reeler mutant mouse. *Vision research* 19, 853-857 (1979). |
| 6. | Tabata, H., Shimizu, N., Wada, Y., Miura, K. & Kawano, K. Initiation of the optokinetic response (OKR) in mice. *Journal of vision* 10, 13-13 (2009). |
| 7. | Benkner, B., Mutter, M., Ecke, G. & Münch, T. A. Characterizing visual performance in mice: an objective and automated system based on the optokinetic reflex. *Behav Neurosci* 127, 788-796 (2013). |
| 8. | van Alphen, B., Winkelman, B. H. & Frens, M. A. Age-and sex-related differences in contrast sensitivity in C57BL/6 mice. *Investigative ophthalmology & visual science* 50, 2451-2458 (2009). |
| 9. | Kretschmer, F., Tariq, M., Chatila, W., Wu, B. & Badea, T. C. Comparison of optomotor and optokinetic reflexes in mice. *Journal of Neurophysiology* 118, 300-316 (2017). |
| 10. | Kretschmer, F., Kretschmer, V., Kunze, V. P. & Kretzberg, J. OMR-arena: automated measurement and stimulation system to determine mouse visual thresholds based on optomotor responses. *PloS one* 8, e78058 (2013). |
| 11. | Prusky, G. T., Alam, N. M., Beekman, S. & Douglas, R. M. Rapid quantification of adult and developing mouse spatial vision using a virtual optomotor system. *Investigative ophthalmology & visual science* 45, 4611-4616 (2004). |
| 12. | Abdeljalil, J. et al. The optomotor response: a robust first-line visual screening method for mice. *Vision research* 45, 1439-1446 (2005). |

FIG. 14
A Correlation between CS (log) and Age in *Rho−/−* Mice
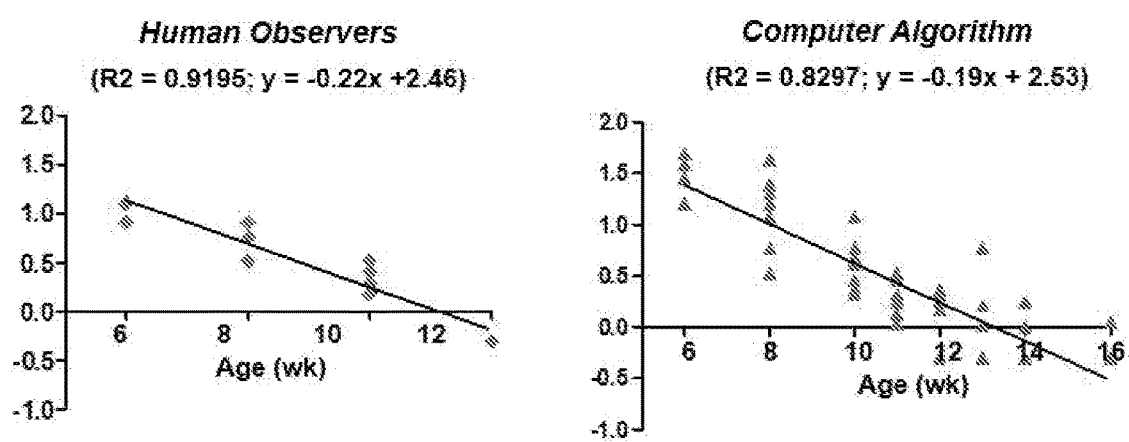
B Correlation between VA and Age in *Rho−/−* Mice
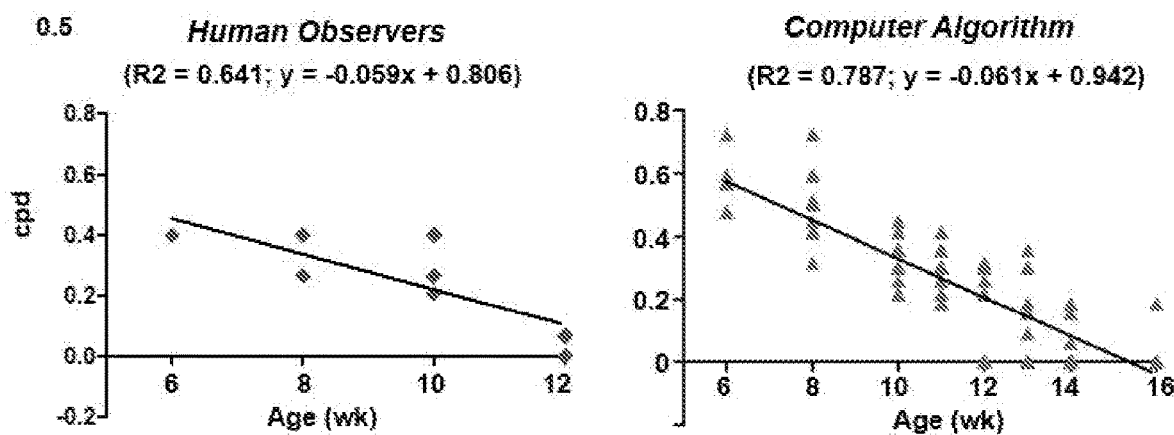

ASSESSING VISUAL FUNCTION

CROSS REFERENCE TO RELATED APPLICATIONS

This application is a U.S. national stage application filed under 35 U.S.C. § 371 of International Patent Application No. PCT/US2019/025618, filed Apr. 3, 2019, which claims the benefit of priority under 35 U.S.C. § 119 (e) to U.S. Provisional Application No. 62/652,282, filed Apr. 3, 2018, the entire contents of which is incorporated herein by reference.

STATEMENT AS TO FEDERALLY SPONSORED RESEARCH

This invention was made with government support under Grant Nos. EY025913, EY025259, EY027067, and EY003790 awarded by the National Institutes of Health. The government has certain rights in the invention.

FIELD

The present disclosure relates generally to devices, methods, and systems for assessing visual function, and more particularly, visual function in animals such as various types of mammals used in research and development of treatments for various eye conditions.

BACKGROUND

Generally, preclinical evaluation of treatment strategies for retinal neurodegenerative diseases is highly dependent on models in small animals, such as mouse models. However, a general lack of surrogate endpoints in animal models that are likely to predict functional benefit for human patients has presented a major challenge in drug development designed to prevent or slowdown vision loss or restore sight. Current methods to assess retinal function in animals include approaches such as electroretinogram, which is a diagnostic test used to measure electrical activity generated by neural and non-neuronal cells in the retina of a test subject in response to light stimuli. These approaches are limited and fail to address concerns relating to visual perception or performance nor the connections between the eye and visual centers.

Rodent pupillary light reflex (PLR) and optomotor reflex (OMR) tests may be sensitive and quantitative assays for evaluating drug actions in the eye and central nervous system. However, existing systems for assessing PLR and OMR in small animals are by visually assessing subtle head movement of rodents upon moving subject stimuli. The assays are difficult to perform and time consuming. Furthermore, the measures are often crude, inaccurate, subjective, and not scalable, especially for behavior phenotyping or drug screening.

Because of these and other reasons, improved devices, methods, and systems are needed.

SUMMARY

The methods, systems, and devices provide a solution to the problems, limitations, and drawbacks of other approaches. Methods, systems and devices are provided herein for assessing visual function in subjects such as human patients, as well as in animals such as various types of mammals used in research and development of treatments for various eye conditions. For example in one exemplary embodiment, an assessment device for assessing visual functions of a test subject is provided that includes a visual stimulus unit configured to display visual stimuli to the test subject. The device also includes at least one input device configured to monitor movement of the test subject, and a processor configured to analyze movement of the test subject taken by the input device and to assess visual functions of the test subject. The visual functions includes at least one of pupillary light reflex or optomotor reflex.

The device can have numerous variations. For example, the visual stimulus unit can include at least one display unit. The input device can include at least one camera, and the camera can include an infrared camera.

In another aspect, an assessment device for assessing optomotor reflex of an animal is provided that includes a visual stimulus unit to display visual stimuli configured to measure visual function of the animal. The device includes a platform configured to place the animal such that the animal can see the visual stimuli. The device also includes an input device oriented to capture images of the animal. The device has a processor that is configured to process images of the animal captured by the camera and configured to assess the visual function by optomotor reflex of the animal based on the processed images. The visual stimuli are configured to change such that the processor can determine the visual function of the animal.

The device can have a variety of embodiments. For example, the visual function can include visual acuity and contrast sensitivity. The visual function can include cone or rod mediated function. The visual stimuli can also include bars that change colors. The visual stimuli can include changing a lumen of the visual stimulus unit. The visual stimuli can include moving black and white bars at predefined widths and speeds and moving at a preset direction of either clockwise or counter-clockwise. The visual stimulus unit can include one or more LCD screens configured to display rotating stripes. The LCD screens can all display black and white bars at a same predefined width moving in one simultaneous direction. In another example, the processor can be configured to assess contrast sensitivity and visual acuity by optomotor reflex protocol based on a head movement count and a staircase reversal count of the animal. The head movement count can include head tracking movements of the animal and head pausing of the animal. Head pausing of the animal can be configured to indicate that the animal cannot see the visual stimuli. The readout of at least one head pause of the test animal indicates an impairment of visual acuity, e.g., the test subject cannot see. The processor can be configured to determine if a head tracking movements count reaches a variable value before a head pausing count reaches one or more times, such as 3 times e.g., at least 2, 3, 4, 5, 10, 15, 20, 25, 50 or more occurrences of a head pause, the variable value, at which point the processor can be configured to determine that the animal can see the visual stimuli. The processor can then be configured to set the visual stimuli at a lower contrast or at a higher spatial frequency. The processor can be configured to determine if a head pausing count reaches one or more times, such as 3 times, a variable value before a head tracking movements count reaches the variable value, at which point the processor can be configured to determine that the animal cannot see the visual stimuli. The processor can then be configured to set the visual stimuli at a higher contrast or at a lower spatial frequency. The input device can include a camera. The camera can include an infrared camera. The processor can be configured to determine an orientation of a head of the animal. In another example, the processor can be configured to determine the orientation based on a contour extraction of the animal, a point of maximum curvature on the contour of the animal, and a computation from the point of maximum curvature and two side points that have equal distance from the point of maximum curvature along the contour.

In another aspect, a method of assessing optomotor reflex of an animal, is provided that includes exposing the animal to visual stimuli configured to measure visual function of the animal. The method also includes taking one or more images of the animal during exposure. The method includes changing the visual stimuli as images are taken, and processing the one or more images to assess the visual function of the animal based on the images.

The method can have numerous variations. For example, the visual function can include visual acuity and contrast sensitivity by optomotor reflex. The visual function can include changing the level of lumens (e.g., brightness) of the screen or of the bar, e.g., to determine photoreceptor rod and cone function. The visual stimuli can include changing color bars, e.g., as a metric to assess color discrimination. The visual stimuli can include black and white bars. The animal can also be unconstrained during imaging. Assessing the visual function of the animal can include assessing head tracking movement in response to the visual stimuli. Assessing head tracking movement can include assessing head pauses by the animal. Processing the one or more images can include assessing the contrast sensitivity and the visual acuity based on a head movement count and a staircase reversal count of the animal. The method can also include determining if a head tracking movements count of the animal reaches a variable value before a head pausing count of the animal reaches 3 times the variable value, and then determining that the animal can see the visual stimuli. The method can then include setting the visual stimuli at a lower contrast or at a higher spatial frequency. In another example, the method can include determining if a head pausing count of the animal reaches 3 times a variable value before a head tracking movements count of the animal reaches the variable value, and then determining that the animal cannot see the visual stimuli. The method can then include setting the visual stimuli at a higher contrast or at a lower spatial frequency.

BRIEF DESCRIPTION OF THE DRAWINGS

The invention will be more fully understood from the following detailed description taken in conjunction with the accompanying drawings, in which:

FIG. 12 illustrates a table of data collected on various exemplary systems and the system of FIG. 2;

FIG. 14A illustrates an example analysis of results comparing the present OMR detection algorithm to human performance; and FIG. 14B illustrates an example analysis of results comparing the present OMR detection algorithm to human performance.

Figure 1:
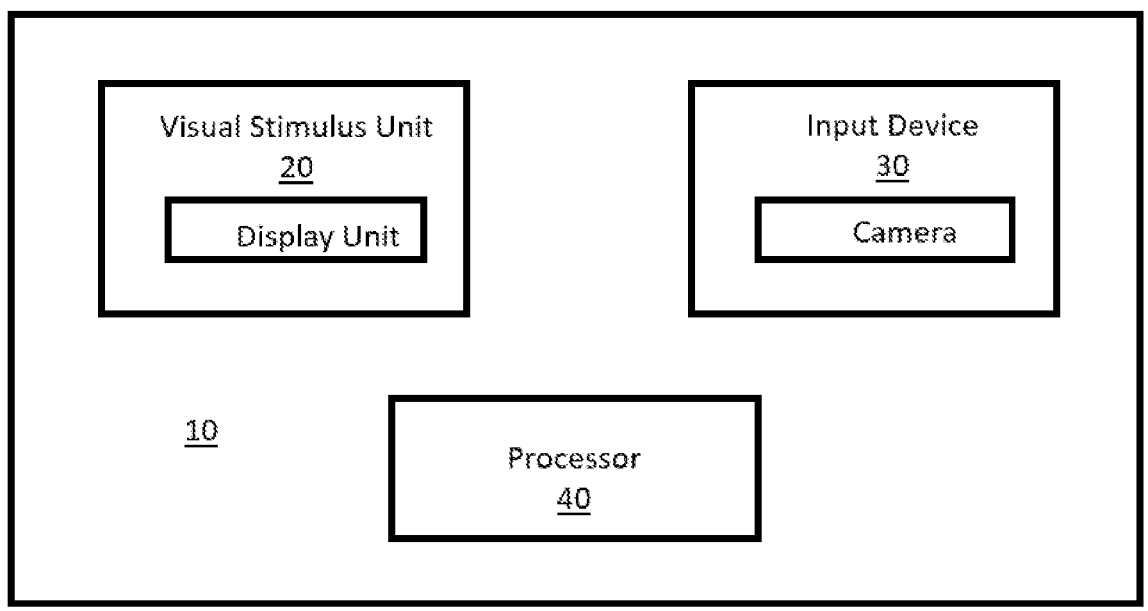
FIG. 1 illustrates an example diagrammatic view of one device configured to assess visual function.

It should be understood that the above-referenced drawings are not necessarily to scale, presenting a somewhat simplified representation of various preferred features illustrative of the basic principles of the disclosure. The specific design features of the present disclosure, including, for example, specific dimensions, orientations, locations, and shapes, will be determined in part by the particular intended application and use environment.

DETAILED DESCRIPTION

The devices and methods of the invention comprise an assessment of head pausing of the test animal, which pausing indicates that the test animal comprises reduced visual acuity and/or that the animal cannot see the visual stimuli. Hereinafter, embodiments of the present disclosure will be described in detail with reference to the accompanying drawings. As those skilled in the art would realize, the described embodiments may be modified in various different ways, all without departing from the spirit or scope of the present disclosure. Further, throughout the specification, like reference numerals refer to like elements.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. The term "coupled" denotes a physical relationship between two components whereby the components are either directly connected to one another or indirectly connected via one or more intermediary components.

It is understood that the term "patient" or other similar term as used herein is inclusive of any subject—human or animal—on which an ocular assessment could be performed. The term "user" as used herein is inclusive of any entity capable of interacting with or controlling a device. The "user" may also be the "patient," or the "user" and "patient" may be separate entities, as described herein.

Additionally, it is understood that one or more of the below methods, or aspects thereof, may be executed by at least one processor. The processor may be implemented in various devices, as described herein. A memory configured to store program instructions may also be implemented in the device(s), in which case the processor is specifically programmed to execute the stored program instructions to perform one or more processes, which are described further below. Moreover, it is understood that the below methods may be executed by a specially designed device, a mobile device, a computing device, etc. comprising the processor, in conjunction with one or more additional components, as described in detail below.

Furthermore, the methods, or aspects thereof, of the present disclosure may be embodied as non-transitory computer readable media on a computer readable medium containing executable program instructions executed by the processor. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

Visual functions such as visual acuity (VA) and contrast sensitivity (CS) are the gold standard for clinical assessment of vision, and they are widely accepted as outcome measures in drug development. As preclinical studies highly depend on mouse models, there is a particular demand on visual performance assays of small animals, such as rodents like mice and rats, that accurately predict human responses. Behaviorally operant methods have been traditionally employed to assess mouse visual functionalities. However, these methods require long-term behavioral training procedures that can take from weeks to months, showing poor scalability for a large number of mice. In contrast, the optokinetic reflex (OKR) or optomotor response (OMR) presents a clinically relevant and readily monitored behavior protocol for visual function tests. OKR/OMR is a stereotyped eye (OKR) or head (OMR) movement in response to movement in the surrounding environment, serving to stabilize the visual image on the retina to allow for high resolution vision. The reflex is highly conserved among vertebrates and does not require a learning process (such as learning to press a lever to get water when seeing a stimulus on the screen in the behaviorally operant methods). OKR/OMR tests have been used to measure VA and CS in rodents by examining eye or head movements tracking rotating stripes. OMR assay is easier to implement for mice compared to OKR, as it requires no constrains to animals, which are allowed to move freely on the platform. Visual assessment of OMR in unrestrained mice by human observers has been reported, yet the OMR scoring is subjective and requires experienced experimenters because the subtle head movements of mice can be easily missed. Semi-automated and fully automated systems for quantifying OMR in unrestrained mice have been attempted by examining head movement in responding to rotating stripes. Fundamental problems of these OMR systems lie in their crude/inaccurate and lengthy scoring procedures. In part, this is because they were designed to detect only positive OMR indicators (i.e., mouse's head movement tracking the rotating stripes) without implementation of any negative OMR indicator, which is supposed to explicitly indicate that the mouse was unable to see the stimuli.

Referring now to embodiments of the present disclosure, assessing PLR and OMR in general, and especially in small animals, is difficult to accomplish. Generally, assessment is performed by visually assessing subtle head movement of rodents upon moving subject stimuli, which results in crude and subjective assessments that are not scalable. Thus provided herein are methods, devices, and systems that are automated and scalable for the measure of small animals' (especially rodents like mice and rats) visual performance, including rodent PLR and OMR, through observation of visual stimuli. One example of a possible algorithm that can be used herein identifies positive OMR indicators that include head tracking behaviors and negative OMR indicators that include head pausing behaviors based on an orientation of a head of a test subject. For example, head tracking behaviors can indicate that the test subject can see visual stimuli, and head pausing behavior can indicate that the test subject cannot see visual stimuli. There can thus be methods, devices, and systems that are configured to use head pausing behavior as a negative OMR indicator, indicating that the test subject cannot see a stimulus, and an optimized staircase testing protocol used to conduct a visual function assessment on the test subject.

The methods, devices, and systems can be configured to be able to serve as processes and tools for a variety of different studies, such as phenotypic studies, as well as for the discovery of new drugs that prevent or slow vision loss and restore sight. For example, methods, devices, and systems are provided herein that include automated platform(s) with system(s) that employ head-movement tracking technique(s) and device(s) designed for small animals, such as rodents, for an unambiguous or less ambiguous evaluation of visual responses, which allows accurate and quantitative assessment of light response and visual perception. This basic approach can also be applied broadly to the evaluation of brain diseases that afflict the visual pathways, including Alzheimer's disease and Autism.

For example, FIG. 1 illustrates a simple diagram of a device 10 for assessing visual functions, such as PLR and OMR, in small animals that includes a visual stimulus unit 20, including one or more display units configured to display various visual stimuli to a test subject; one or more input devices 30 that include at least one camera that is configured to monitor movement of the test subject (for example, taking one or more images and/or videos); and a processor 40 that is configured to analyze the movement of the test subject taken by the input device (such as the camera) and to assess visual functions of the test subject, and the device can be used in a system including a designated general location for the test subject in which the test subject can see the visual stimulus unit and move freely while being monitored by the camera. It should be noted that the architecture depicted in FIG. 1 is simplified and provided merely for demonstration purposes.

Figure 2:
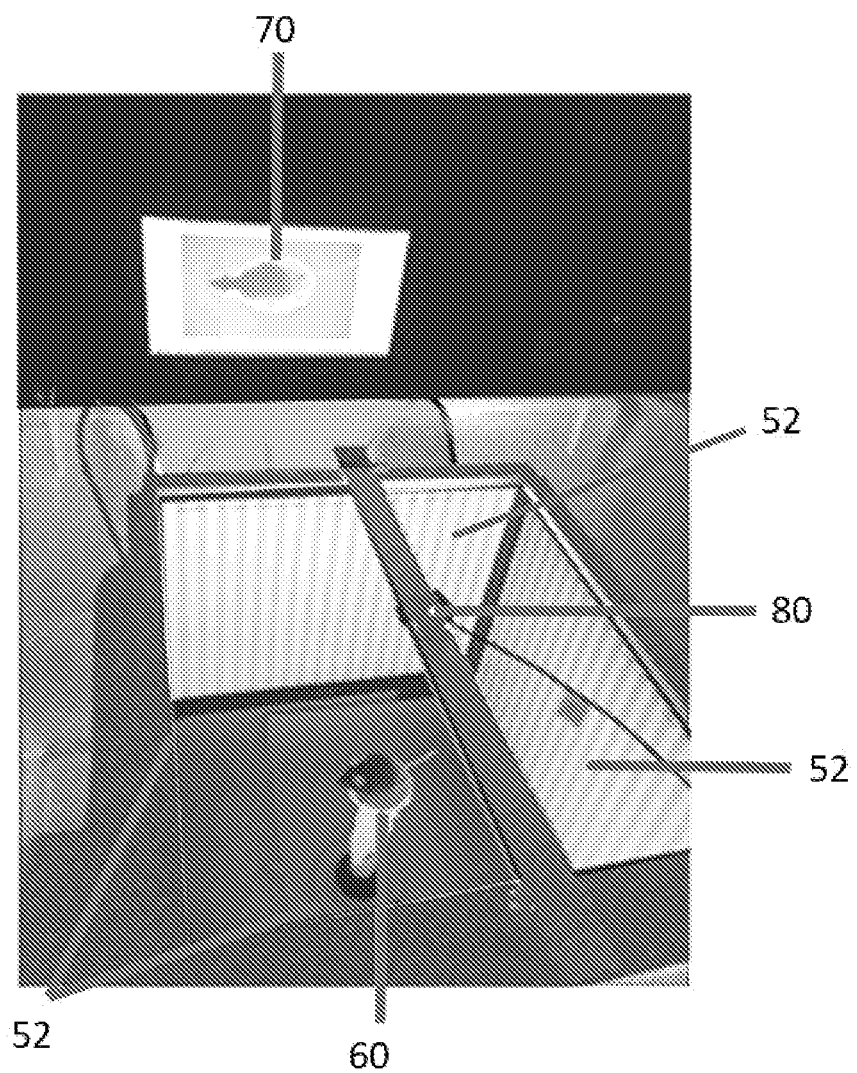
FIG. 2 illustrates a system with another device configured to assess visual function.

FIG. 2 illustrates another example of a system for OMR assessment in small animals, such as mice. The system includes a visual stimulus unit to display visual stimuli configured to measure visual acuity and contrast sensitivity. For example, the visual stimulus unit can include displaying various visual stimuli on one or more displays or screens 52, such as 4 LCD screens, that can be configured to enclose a central area. Typical visual stimuli to be displayed can include black and white and/or color bars or stripes. The bars can be moving and/or rotating, and they can have defined widths and/or speeds and/or can move in a set direction, such as clockwise or counter-clockwise. The one or more bars used as visual stimuli can also change colors during display. The screens 52 can all display black and white and/or color bars at the same defined width moving in one simultaneous direction. By changing the width and contrast, the system can determine the visual acuity and contrast sensitivity of the test subject. Furthermore, the system can change lumens of one or more of the screens 52 such that the system can determine cone or rod mediated function. The system can also include a small animal holder platform 60 in the middle of the enclosed area, which allows the small animal (such as the mouse shown in FIG. 2) to stand and move freely such that the animal is unconstrained during testing. In such a situation, assessing the visual function of the animal can thus include assessing head tracking movement in response to the visual stimuli, and assessing head tracking movement can include assessing head pauses by the animal that indicate that the animal cannot see the visual stimuli. The system can include a processor such as a computer 70 running an OMR detection algorithm (discussed in detail below) to process mouse images captured by a camera 80 mounted above the platform 60.

Figure 3:
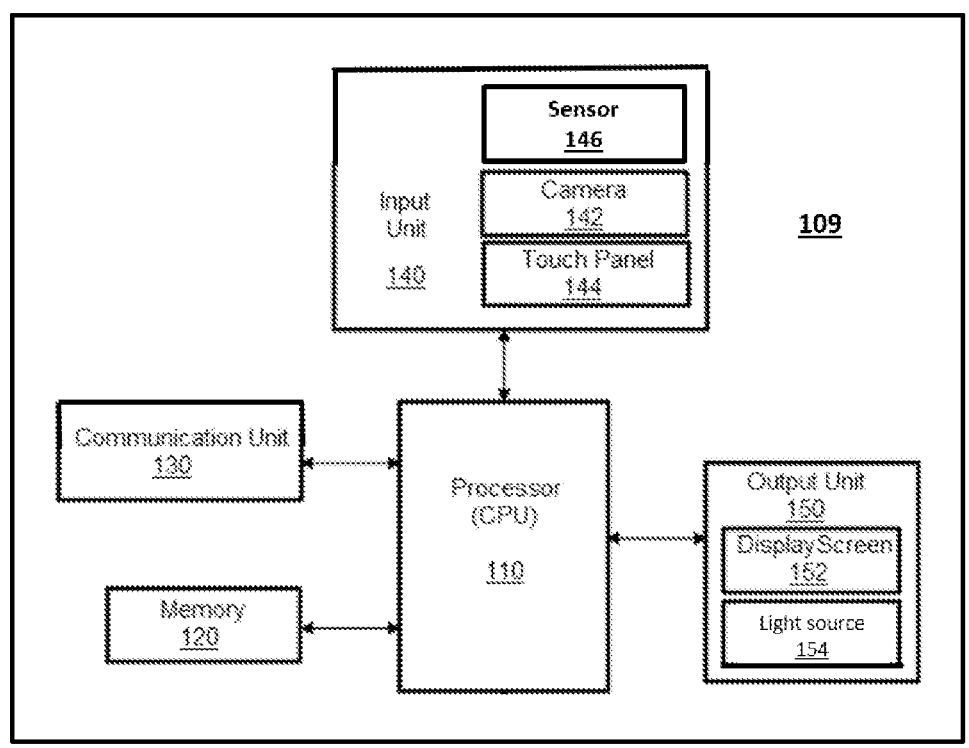
FIG. 3 illustrates an example diagrammatic view of a device architecture.

While specific devices and systems are discussed above, a variety of devices and arrangements can be used herein. FIG. 3 illustrates an example diagrammatic view of an exemplary device architecture according to embodiments of the present disclosure. As shown in FIG. 3, a device 109 may contain multiple components, including, but not limited to, a processor (e.g., central processing unit (CPU) 110, a memory 120, a wired or wireless communication unit 130, one or more input units 140, and one or more output units 150. It should be noted that the architecture depicted in FIG. 3 is simplified and provided merely for demonstration purposes. The architecture of the device 109 can be modified in any suitable manner as would be understood by a person having ordinary skill in the art, in accordance with the present claims. Moreover, the components of the device 109 themselves may be modified in any suitable manner as would be understood by a person having ordinary skill in the art, in accordance with the present claims. Therefore, the device architecture depicted in FIG. 3 should be treated as exemplary only and should not be treated as limiting the scope of the present disclosure.

The processor 110 is capable of controlling operation of the device 109. More specifically, the processor 110 may be operable to control and interact with multiple components installed in the device 109, as shown in FIG. 3. For instance, the memory 120 can store program instructions that are executable by the processor 110 and data. The process described herein may be stored in the form of program instructions in the memory 120 for execution by the processor 110. The communication unit 130 can allow the device 109 to transmit data to and receive data from one or more external devices via a communication network. The input unit 140 can enable the device 109 to receive input of various types, such as audio/visual input, user input, data input, and the like. To this end, the input unit 140 may be composed of multiple input devices for accepting input of various types, including, for instance, one or more cameras 142 (i.e., an "image acquisition unit" that can include any variety of cameras, such as infrared and other low-light cameras, standard-light cameras, etc.), touch panel 144, microphone (not shown), sensors 146, one or more buttons or switches (not shown), and so forth. The input devices included in the input 140 may be manipulated by a user. Notably, the term "image acquisition unit," as used herein, may refer to the camera 142, but is not limited thereto. The output unit 150 can display information on the display screen 152 for a user and/or a test subject to view. The display screen 152 can also be configured to accept one or more inputs, through a variety of mechanisms known in the art. The output unit 150 may further include a light source 154.

The device 109 can thus be programmed in a manner allowing it to be configured to assess visual functions, such as PLR and OMR, in small animals, as described herein.

Figure 4:
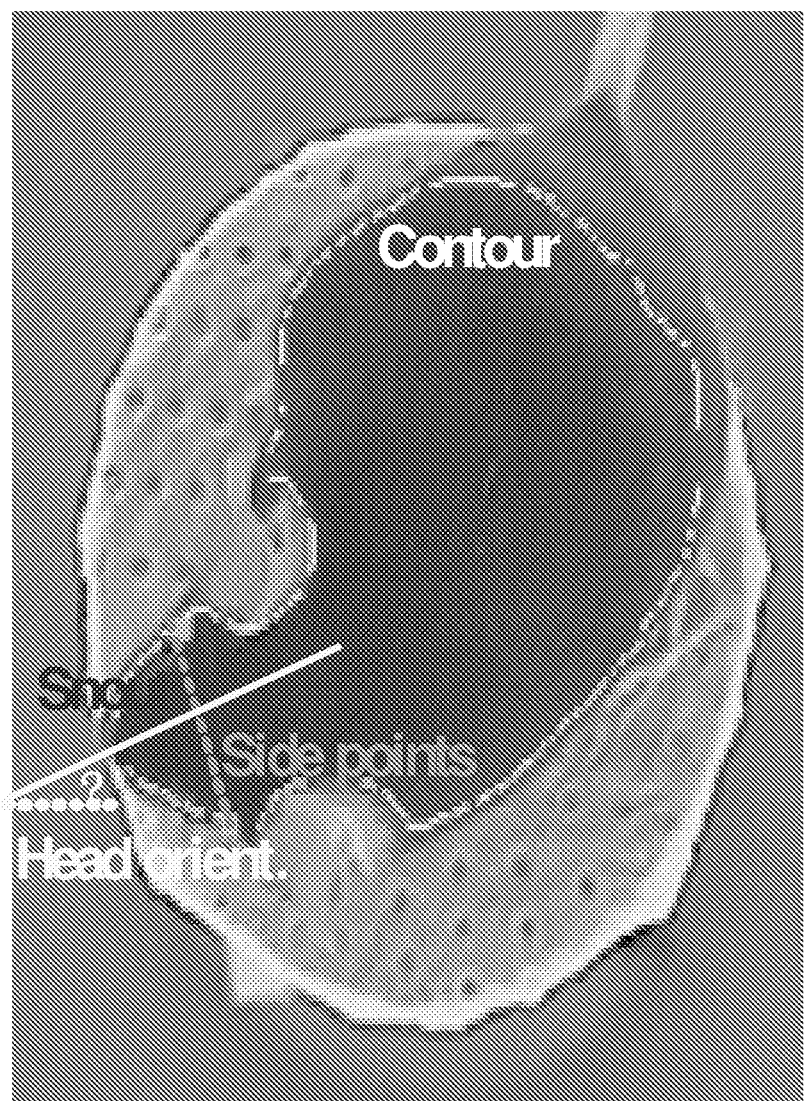
FIG. 4 illustrates an example screen shot of the system of FIG. 2.

As one or more image acquisition unit (such as the cameras discussed above) acquires image(s) and/or video(s) of the test subject, the one or more processor(s) as discussed above can process the acquired images in a variety of ways to assess visual functions of the test subject. For example, FIG. 4 illustrates a representative screen shot taken from the one or more processors. The screen shot in FIG. 4 illustrates an example taken from the computer 70 running an OMR detection algorithm, but similar software and algorithms can be used on any of the processors discussed herein. The illustrated algorithm flags positive OMR indicators (head tracking behaviors) and negative OMR indicators (head pausing behaviors) based on the dynamics of a test subject's orientation, such as the mouse used herein. The head orientation is calculated in three steps, as illustrated on FIG. 4: 1) mouse contour extraction, 2) Locating the snout as the point with the maximum curvature on the contour, and 3) head orientation computation from the snout point and two side points that have equal distance from the snout along the mouse contour.

Figure 5:
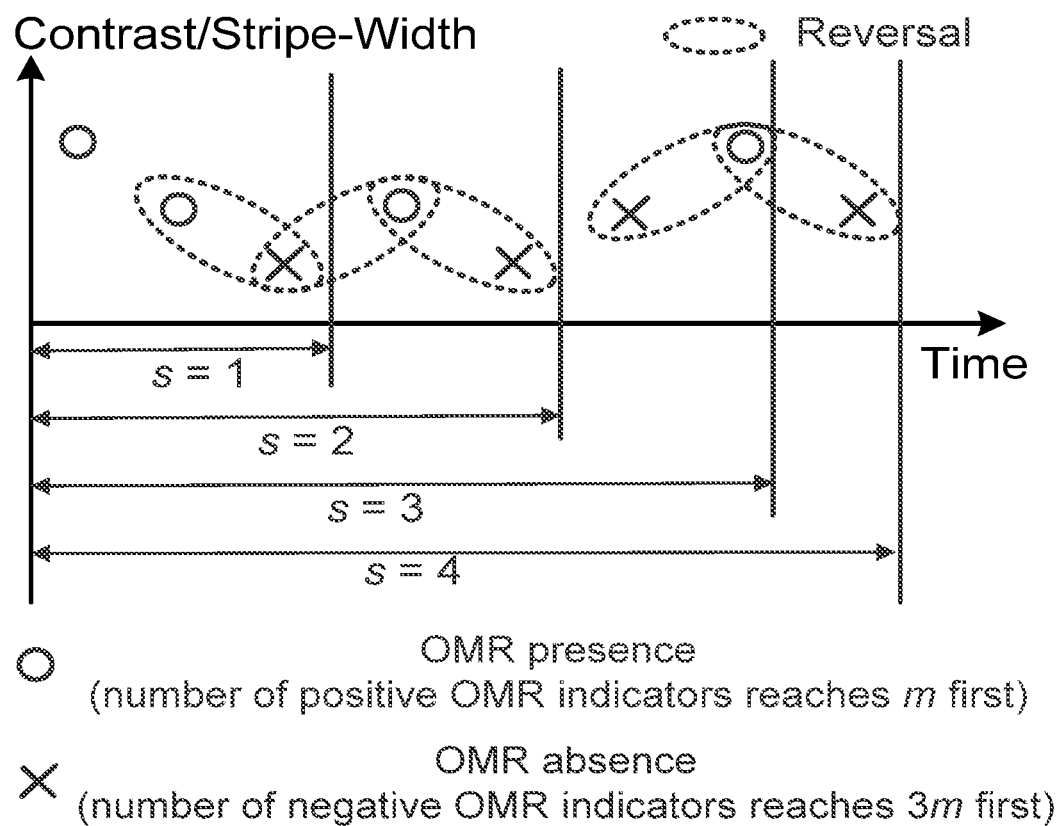
FIG. 5 illustrates an example analysis of results of the system of FIG. 2.

The protocol run on the results illustrated herein include a staircase protocol that is implemented for CS and VA assessment by OMR. The CS herein is defined as the reciprocal of the lowest contrast perceivable, and the VA is defined as the highest spatial frequency perceivable. The protocol is characterized by two parameters: 1) head movement count m, and 2) staircase reversal count s. FIG. 5 illustrates the schematic for the staircase protocol run herein for CS and VA measurements. If the count of positive OMR indicators (head tracking movements) reaches m before the count of negative OMR indicators (head pausing count and/or status) reaches one or more times the head movement count m (for example, 2 m, 3 m, 4 m, 5 m, etc.), the protocol asserts an OMR presence (implying that the test subject, such as the mouse, is able to see the stimuli), and sets the stimulus one level harder, i.e. at a lower contrast (for CS assessment) or at a higher spatial frequency (for VA assessment). When the count of negative indicators reaches one or more times the head movement count m (for example, 2 m, 3 m, 4 m, 5 m, etc.) before the count of positive ones reaches m, the protocol asserts an OMR absence (implying that the test subject, such as the mouse, fails to see and/or cannot see the stimuli), and sets the stimulus one level easier, i.e. at a higher contrast (for CS assessment) or at a lower spatial frequency (for VA assessment). Thus a larger number of positive OMR indicators (such as head tracking movements) indicates that the test subject can see the stimuli, while a larger number of negative OMR indicators (such as head pausing by the test subject) indicates that the test subject cannot see the stimuli. The count of trial reversals between one OMR presence and one OMR absence has to reach the staircase reversal count s before a conclusive final vision measurement. While this specific algorithm is provided herein, a variety of different approaches and protocols can be used. Some additional protocols are discussed below, but the protocol used herein is not limited to these specific examples and instead can include any algorithms used to assess visual functions of the test subject. Additionally, specific types of mice and specific age ranges are discussed below. However, the exemplary protocol discussed herein can be applied to any types of animals, such as other types of mice, other mammals, and/or other animals used during research and development of various treatments for eye conditions for eventual application to humans, and various ages of mice can be used, such as 1 week olds, 2 week olds, 3 week olds, 4 week olds, 5 week olds, 6 week olds, 7 week olds, 8 week olds, 9 week olds, 10 week olds, 0-3 year olds, etc.

Optimization on Optomotor Response—Based Visual Function Assessment:

A specific optimization process is provided herein to determine a possible OMR detection algorithm. However, a variety of different approaches can be taken, and the specific optimization process discussed below is for exemplary purposes. The process of data analysis used herein involved two stages: the first stage was determining a beneficial staircase protocol to allow the achievement of best accuracy with minimal time consumption, using the CS assessment. The second stage validated the feasibility of the exemplary protocol by applying it to both CS and VA assessments, thus representing a present OMR detection algorithm that can be used instead of human detections that will provide better results while being faster than human detections.

Figure 6:
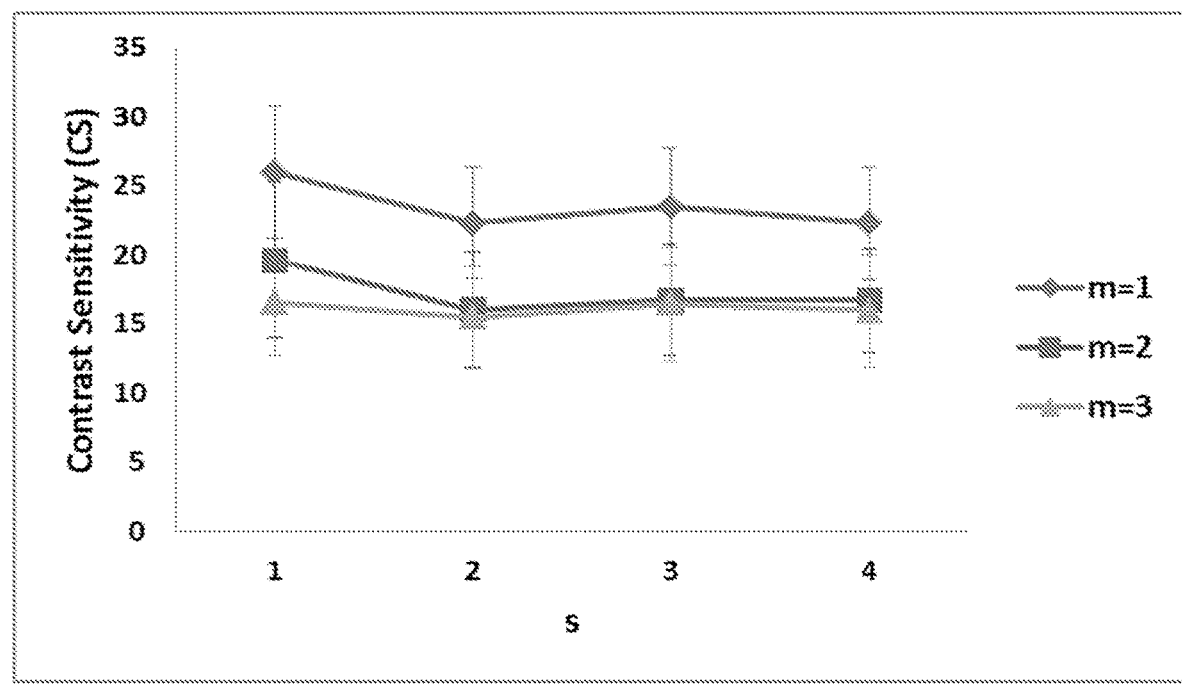
FIG. 6 illustrates an example analysis of results of the system of FIG. 2.
Figure 7:
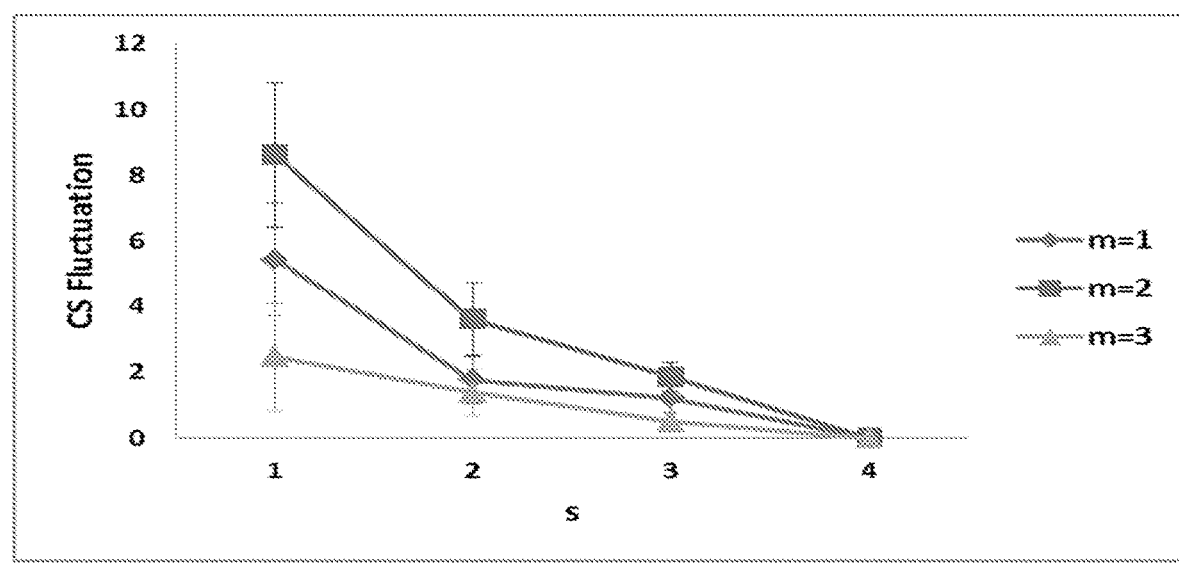
FIG. 7 illustrates an example analysis of results of the system of FIG. 2.
Figure 8:
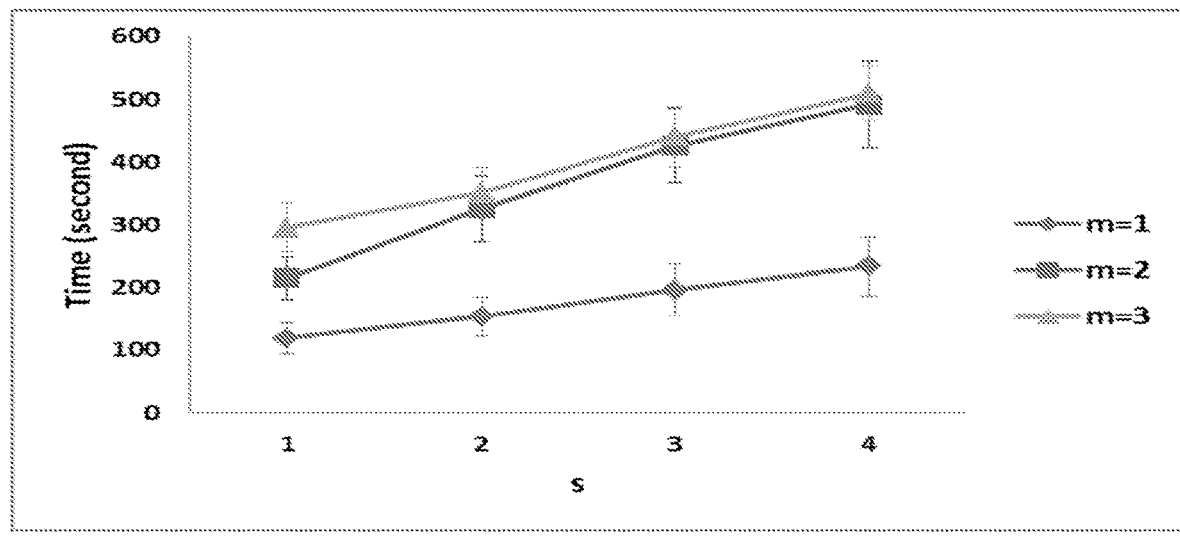
FIG. 8 illustrates an example analysis of results of the system of FIG. 2.

To select a staircase protocol, 12 staircase protocols were tested with different combinations of head movement count m (m=1, 2, or 3) and staircase reversal count s (s=1, 2, 3, or 4), and their measurement reliability and time consumption were compared in 9 WT mice (approximately 6 to 8 weeks old) and 3 Rhodopsin knockout (Rho$^{-/-}$—representing a genetically modified mouse strain that carries Rhodopsin deficiency) mice (approximately 6 weeks old). An analysis of variance (ANOVA) that was determined through use of three m values by four s values revealed that neither m nor s significantly altered the CS value (p=0.269, $F_{2,20}$=1.403 for m, and p=0.361, $F_{3,30}$=1.108 for s) (for example, as illustrated in FIG. 6). Although the average CS seemed to be higher when m=1 than when m=2 or 3, a post-hoc test did not find any significant difference between these groups in pairwise comparisons (p=0.660 for m=1 vs 2, and p=0.685 for m=1 vs 3). CS fluctuation for protocol (m, s), defined as the absolute difference between the CS measured with (m, s) and the CS measured with (m, 4) (used as reference), however, significantly decreased with m (p=0.043, $F_{2,20}$=3.707) and s (p<0.001, $F_{3,30}$=10.457) (FIG. 7). As expected, time consumption of each test significantly increased along with m (p=0.001, $F_{2,20}$=10.628) and s (p<0.001, $F_{3,30}$=51.462) (for example, as illustrated in FIG. 8). A much larger increase in time consumption was noted when m increased from 1 to 2. In contrast, the time reduction with decreasing s was relatively small. As illustrated in FIGS. 6-8, the data suggest that while varying either m or s does not significantly change the CS value, increasing m reduces CS fluctuation or improves reliability at a significant cost of time. In contrast, increasing s significantly reduces CS fluctuation with a relatively small impact on time consumption.

To select the optimal combination of parameters m and s, the 12 protocols were ranked in an ascending order based on CS fluctuation and time consumption, respectively. Each protocol was scored by the sum of its ranks in both orders. The median score was 13.5 and the interquartile range was from 12 to 15. Intuitively, protocols with lower scores would be preferable because they represent small CS fluctuations and short time consumption. Among the 12 protocols, three were scored below the interquartile range. They were (m, s)=(1, 4), (1, 3) and (1, 2), with a score of 6, 8, and 9, respectively. All protocols with m=1 yielded good scores, mainly because of their time saving effects. As the CS fluctuation was not very different among the 3 protocols (0, 1.2, 1.77 for s=4, 3, 2, respectively), s=2 was most favorable because of its larger advantage on shorter time consumption (234 s, 196 s, 154 s for s=4, 3, 2, respectively); therefore, the selected values were (m, s)=(1, 2) as the optimal protocol in the following validation experiment. Again, while these specific values were used for the experiment below, a variety of other values of m and s are possible, such as 1, 2, 3, 4, 5, 6, etc., depending on various considerations when selecting values, such as desired time consumption and acceptable CS fluctuation.

FIGS. 6-8 thus illustrate CS values, CS fluctuation, and time consumption of different staircase protocols. Data were collected from 12 mice, including 9 WTs and 3 Rho$^{-/-}$. Repeated measures of ANOVA tests revealed that varying neither m nor s caused significant change in the CS values. The CS fluctuation for the protocol (m, s) in FIG. 7 is defined as the absolute difference between the CS measured with (m, s) and the CS measured with (m, 4) (used as a reference). CS fluctuation significantly decreased and time consumption significantly increased along with increasing values of m and s, respectively. Error bars illustrated in FIGS. 6-8 represent standard error of the mean (S.E.M.) values.

Figure 9:
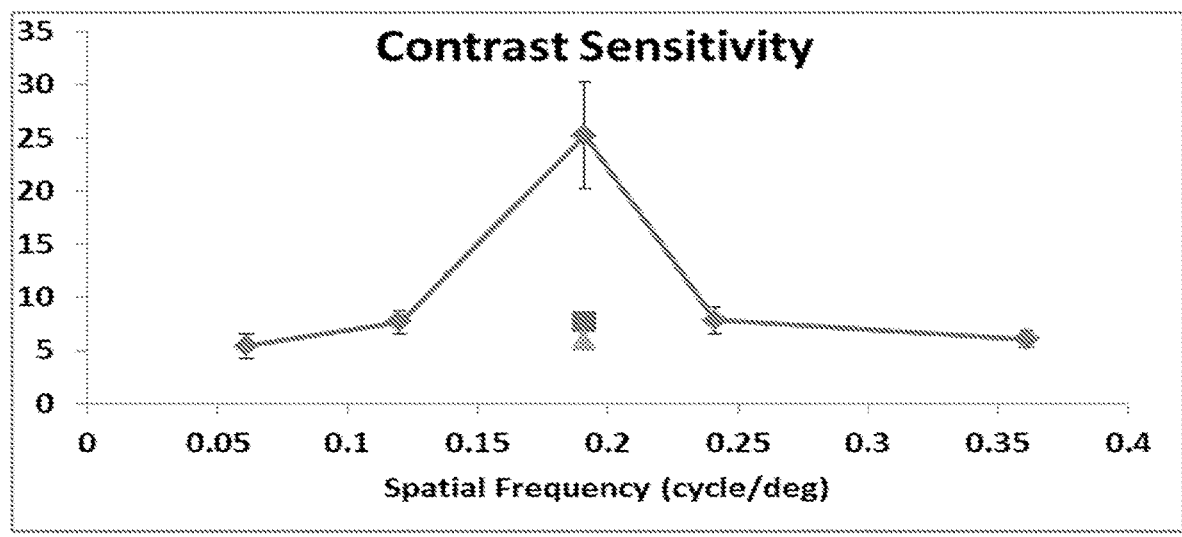
FIG. 9 illustrates an example analysis of results of the system of FIG. 2.

The feasibility of the optimal protocol for CS and VA assessments was verified using another 10 WT mice and 11 Rho$^{-/-}$ mice. The CS and VA values were tracked in Rho$^{-/-}$ mice from the age of approximately 6 weeks onward to follow the visual function changes along the course of their photoreceptor degeneration. Generally, WT mice have developed mature and stabilized vision by the age of approximately 6 weeks, while Rho$^{-/-}$ mice are reported to undergo progressive photoreceptor degeneration from approximately 24 days onward and retinal function abnormality (as determined by electroretinogram) from approximately 7 weeks onward that will eventually lead to blindness by approximately 4 months old. The progressive loss of photoreceptors and visual functions in Rho$^{-/-}$ mice are well documented. As the strength of OMR responses is sensitive to spatial frequency, mouse CS with OMR were assessed under varied spatial frequencies. For example, FIG. 9 illustrates that the CS of WT mice at the age of approximately 6 weeks peaked at approximately 0.19 cycles per degree (cpd). Two CS outlier data points (represented by the single triangle and square in FIG. 9) at this spatial frequency were excluded from data analysis because they were abnormally lower than the two mice's CS values at neighboring frequencies. These results showed higher sensitivity of the present protocol in assessing CS in mice than what was previously reported using other methods, such as illustrated in FIG. 12 and discussed below.

Figure 10:
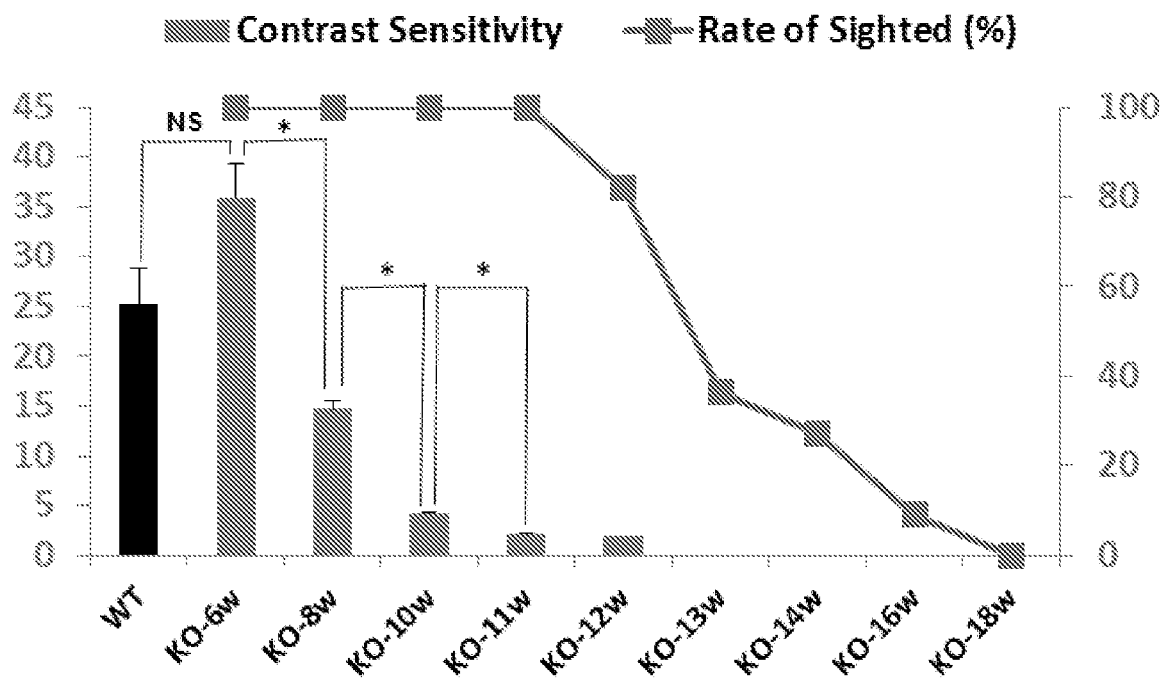
FIG. 10 illustrates an example analysis of results of the system of FIG. 2.

The change of peak CS value was also tracked (measured at the peak spatial frequency of 0.19 cpd) in Rho$^{-/-}$ mice from approximately 6 weeks onward. The average peak CS value of WT and Rho$^{-/-}$ mice at approximately 6 weeks showed no significant difference, as shown in FIG. 10 (25.2 for WT and 35.9 for Rho$^{-/-}$, p=0.10, t-test). As expected, the peak CS value of Rho$^{-/-}$ mice dropped gradually after the age of approximately 6 weeks; by the age of approximately 8 weeks, it had already dropped substantially to approximately 15. The rate of sighted mice, which is defined as the percentage of mice with a measurable CS, was calculated. While all Rho$^{-/-}$ mice had detectable OMR by the age of approximately 10 weeks, over half of Rho$^{-/-}$ mice showed no measureable CS by the age of approximately 13 weeks, suggesting that half of these mice were blind. Average peak CS was calculated only for mice with measureable CS, and the average was not reported when the rate of sighted fell below 50% in FIG. 10.

Figure 11:
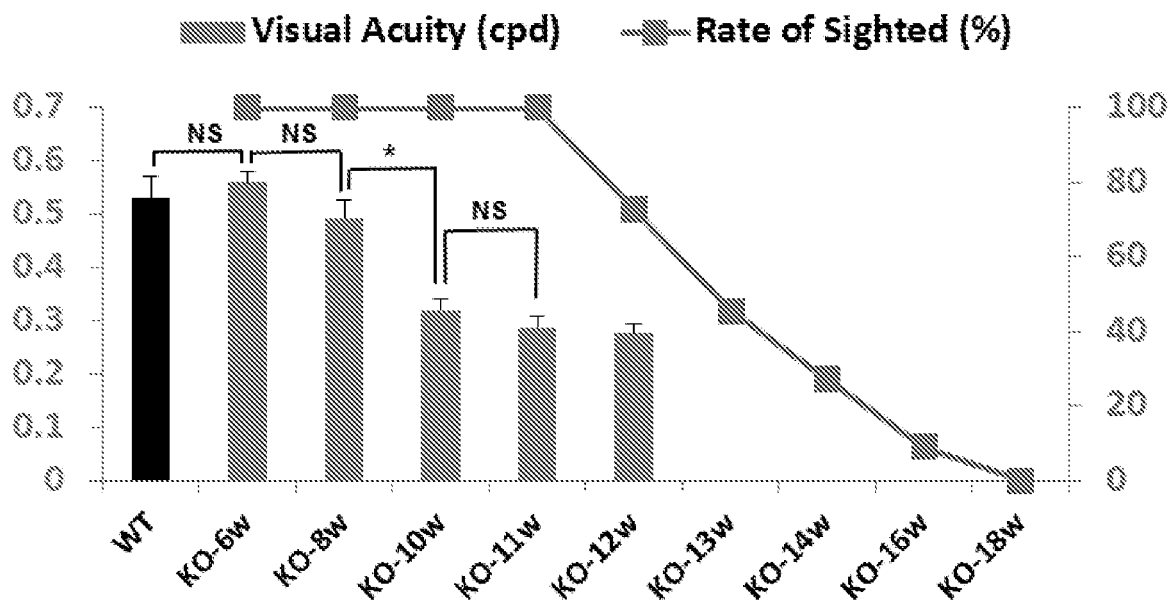
FIG. 11 illustrates an example analysis of results of the system of FIG. 2.

The VA value was then assessed in WT and Rho$^{-/-}$ mice. The VA of Rho$^{-/-}$ mice at the age of approximately 6 weeks were comparable with that of WT mice (0.53 cpd for WT and 0.56 cpd for Rho$^{-/-}$, p=0.665, t-test), and it also started to drop from approximately 8 weeks onward, albeit not as drastically as seen in the CS assessment (FIG. 11). The rate of sighted mice, as calculated by the percentage of mice with a measurable VA, was about the same as that obtained using the CS assessment in FIG. 10. By the age of approximately 13 weeks, more than half of Rho$^{-/-}$ mice showed no measureable VA. By the age of approximately 18 weeks, no Rho$^{-/-}$ mice showed measurable VA, or in other words, they all became blind. This rate-of-sighted curve measured by VA matches perfectly with that measured by CS assessment. Similarly, the average VA was not reported when the rate of sighted fell below 50% in FIG. 11.

Although the presently discussed algorithm used constant display of visual stimuli, the CS and VA values obtained were manually checked using either the constant display or the short display and found no obvious difference between these two methods. OMR was clearly observed in mice exposed to constant display (or short display) of stimuli throughout the experiment. In addition, CS and VA values were assessed in white colored Balb/c mice. In agreement with what has been observed by others, Balb/c mice responded to the rotating grates by moving their head toward an opposite direction against the rotating bars following stimuli. The OMR detection program was thus reconfigured to track head motion against the direction of the rotating stimuli. Resultant CS of 3.078±0.720 and VA of 0.476±0.063 were detected from adult Balb/c mice, consistent with that reported. Together, the results demonstrate rigorous and consistent data of CS and VA assessments by the present OMR detection algorithm.

Thus FIG. 9 illustrates a CS assessment in WT mice. CS of WT mice at the age of approximately 6 weeks (n=10) were measured by our OMR system at 5 different spatial frequencies using the optimal protocol representing the present OMR detection algorithm. Two CS outliers (labeled as single triangle and square) at the peak spatial frequency of 0.19 cpd were excluded from data analysis, as they were abnormally lower than the two mice's CS at neighboring frequencies. FIGS. 10 and 11 illustrate tracks of CS and VA in WT and Rho$^{-/-}$ mice of various ages. Peak CS at the spatial frequency of 0.19 cpd (a) and VA (b) in 6-week-old WT (black bar, n=8) and 6-18 week-old Rho$^{-/-}$ mice (KO; blue bars, n=11) were measured using the optimal protocol. The rate of sighted mice was calculated as the percentage of Rho$^{-/-}$ mice with measurable CS/VA. Average CS/VA was calculated only for mice with measureable CS/VA, and the average is not reported when the rate of sighted fell below 50%. In FIGS. 10 and 11, Error bars represent S.E.M. An asterisk * denotes statistical significance. The notation NS denotes no statistical significance. For other pairs not connected, statistics analyses were not shown for clarity, or could not be performed properly as we stopped tracking completely blind mice.

In this study, a negative OMR indicator, mouse head pausing status, was employed to replace the arbitrarily pre-set time window or blind mouse's OMR baseline as used in previous studies. When this negative indicator was applied in combination with a positive OMR indicator (the head tracking state in response to visual stimuli), implementation was possible of an unambiguous, fast staircase protocol to assess visual functions in WT and Rho$^{-/-}$ mice. The staircase protocol characterized by head movement count m=1 and staircase reversal count s=2 is a setting that provides beneficial results considering accuracy and efficiency for vision function assessments. This exemplary protocol enables quick measurements of visual functions in mice with normal or impaired vision. The entire procedure required less than 3 minutes per mouse (FIG. 8). No mice were trained or hand-picked by any means, while this was usually done in operant studies. The protocol can be easily implemented into a completely automated system.

The results of CS, VA, and peak spatial frequency of stimuli at which peak CS or equivalent response was obtained are in agreement with those in the literature (for example, as illustrated in the table provided in FIG. 12, including a legend below the table identifying each work provided in the table, and further explored in Shi et al., Optimization of Optomotor Response-based Visual Function Assessment in Mice, Scientific Reports, which is incorporated herein by reference in its entirety). Using the present OMR detection algorithm, the measured VA (0.53 cpd) and peak frequency (0.19 cpd) are within the reported range (approximately 0.4 to 0.6 cpd and approximately 0.1 to 0.2 cpd, respectively). The CS results (25 for WT mice and 35 for 6-week-old Rho$^{-/-}$ mice) are at the high end of the reported CS range, suggesting a high sensitivity of the exemplary protocol provided herein. Only two papers reported CS value higher than those found with the exemplary protocol provided herein. First, Histed et al. reported CS of 50 from the 3 most well-behaved animals they hand-picked from 21 mice. Their findings thus appear to be biased towards animals with a better vision. In contrast, all of the 33 mice tested in the exemplary results provided herein were randomly picked and shipped directly from Jackson Laboratory without any filtering process, thus they included individual variability. Some mice in the present results indeed showed a CS of 50. Second, Van Alphen et al. also reported an extremely high CS of 100 and peaked at 0.17 cpd. As this is by far the only study reporting such a high CS level, which is about the same as human eyes, the findings need further confirmation to verity such abnormal result. Overall, the method provided herein using the present OMR detection algorithm was shown to be able to measure mouse CS with a high sensitivity and in a quick, efficient manner.

As summarized in FIG. 12, the VA results based on the exemplary protocol provided herein were similar to findings using operant methods as well as that using the electrophysiology methods. For example, VEP has been used to evaluate visual physiology that has a counterpart in visual behavior, including VA and CS, in mice. Both invasive (with intracortical electrodes) and non-invasive procedures of VEP recording in conscious mice reported similar visual acuity (0.60±0.15 and 0.62±0.156 cpd, respectively) in normal C57BL/6J mice. In general, many of the previous OMR methods reported a lower VA (except that by van Alphen et al., who also reported an extremely high CS value and thus suggest further confirmation is required) than the operant methods. These results may be due to the lack of a precise negative OMR indicator. As Kretschmer et al. showed, mouse's OMR responses become less obvious as visual stimuli are weaker (i.e. smaller OMR gain). When the stimulus approaches to the visual threshold, the weak OMR may be mixed with many other voluntary head movements, thereby leading to premature conclusion of a visual threshold. Implementation of negative OMR indicators ignoring voluntary head movements in the present exemplary protocol thus allowed for applying a staircase protocol to accurately pinpoint the visual thresholds. Since visual function assessment can be based on finding the threshold, staircase testing has advantages over other methods relying on arbitrary baselines by focusing on the visual thresholds to acquire more accurate and reliable results. Moreover, focusing on thresholds greatly saves testing time on easily visible stimuli. Thus, the exemplary protocol provided herein provides substantial benefits over those used in the art.

The physiological mechanism of the head pausing behavior may speculate that it may implicate that the mouse is attending to the screen, similarly to meerkats watching for predators. Since OMR is an involuntary behavior when mouse sees the stimuli, head pausing indicates that the mouse may be trying to look but cannot detect the moving stimuli. While Kretschmer et al. used random and voluntary head movements of mice to calculate OMR baseline, this approach may be inappropriate to be taken into consideration for vision assessment. For instance, rodent head bobbing (swaying head from side to side) is believed to be a behavior that allows the animal to acquire depth perception because such movement can create visual parallax. An unstill head can also be a sign of animal incompliance, or environment exploring with other sensory modules.

Thus the present results suggest that CS is a more sensitive indicator for vision loss than VA in $Rho^{-/-}$ mice, especially at the early stage of retinal degeneration. From ages of approximately 6 to 8 weeks, CS in $Rho^{-/-}$ mice dropped from 36 to 15 (as illustrated in FIG. 10), an average 59% reduction, while VA dropped only from 0.56 to 0.49 cpd (as illustrated in FIG. 11), merely a 12.5% reduction on average. This result is in line with the findings from clinical studies in human patients. Kleiner et al. found that CS is useful for measuring visual loss not detected by standard Snellen charts in patients with macular degeneration. These data suggest that measuring CS in animal models is highly relevant to preclinical research, such as research being done to assist or treat various eye conditions such as macular degeneration in humans.

While $Rho^{-/-}$ mice do not have rod function since birth, their cone degeneration typically starts from postnatal week 7, as electrophysiology study by Jaissle et al. showed. They also showed that no clear ERG signal was detectable after postnatal week 13 under photopic conditions. Our data are consistent with their findings. The time course of photopic vision loss in $Rho^{-/-}$ mice is similar to human beings with retinitis pigmentosa, who first develop night blindness followed by central vision loss or even complete blindness. Therefore, using the $Rho^{-/-}$ model to evaluate measurement of CS and VA under photopic conditions is appropriate.

The results included non-hand-picked mouse subjects (total n=33 in both experimental stages, including WT as well as $Rho^{-/-}$ mice), and followed up on the visual functions of 11 $Rho^{-/-}$ mice from 6 to 18 weeks in their postnatal lives. Observation was made of large individual variations in visual functions among the WT as well as $Rho^{-/-}$ mice. Some $Rho^{-/-}$ mice became blind at the age of 12 weeks, while other showed measureable vision until the age of 18 weeks. At the age of 6 weeks, there was a wide range of CS (from 10 to 50) in the sample. Such large between-group variabilities underscore the importance of within-group study designs, in which individual differences can be canceled by each individual subject and therefore statistical power can be achieved with relatively small sample sizes. By measuring mice efficiently over long time course without many compromises due to, for example, training, stress, and anesthesia, demonstration was made of the potential of the exemplary protocol and method for medical research involving small animals that can then be translated to human conditions.

This OMR system can be extended to other mouse models in the future. For instance, OMR assessments in mice with various retinal cell defects, including primary cone pathology and/or ganglion cell pathology, may be valuable. Also, implementation of an infrared image camera would allow evaluation of mouse head movements under a dim light. As shown using white colored Balb/c mice, the current OMR detection algorithm is effective for animals of other colors, as long as a good color contrast between the mouse skin color and the background of the platform is provided. Finally, while the present OMR detection algorithm used constant display of visual stimuli, there was no obvious differences in the mouse OMR elicited by either constant or short displays of stimuli. However, in experiments with a short display of stimuli, mice often responded to the on and off of the display by a stalling (pausing) behavior, which may complicate the program design and thus can be taken into consideration when addressing the exemplary protocol provided herein if such a use is desired. Such a response of animals can be considered and incorporated into any OMR detection algorithm based on the present protocol if a short display of stimuli is desired with the present OMR system.

Exact Experimental Protocols Used:

Detailed specifics of tests performed and results obtained are discussed below. However, the approach to determining protocols and the present OMR detection algorithm discussed above can be implemented in a variety of ways and should not be limited to the discussed arrangement below. For automated and unbiased assessment of visual behavior in mice, an OMR system was built, which was comprised of three units, as shown in FIG. 2. A visual stimulus unit with four LCD screens (Acer 15") was used for displaying rotating black-and-white stripes. The luminance of the screen was calibrated using a luminance meter (Minolta LS-100). The width, direction and contrast of stripes were configurable and manually set during the experiments depending on the mouse's response. A platform was set in the middle of the arena for mouse to stand and move freely on. A computer vision unit based on a desktop computer (Intel i7-4790 CPU @ 3.60 GHz) was running a house-made OMR detection algorithm to process the real-time mouse images captured by a 30 frames/sec (fps) camera mounted on top of the platform. The algorithm extracted and smoothed the contour of the mouse body, and then located the mouse snout as the maximum curvature point on the contour (FIG. 2). Two head-side points with equal distance to the snout point along the contour were also identified. The distance was a fixed fraction with respect to the length of the mouse contour. The mouse head orientation ($\theta$ in FIG. 4) was computed as the orientation of the line that connected the snout point and the mid-point of the two head-side points (the yellow line in FIG. 4). The snout coordinate trajectory was also recorded. Signals of head orientations and snout coordinate trajectory were filtered to remove motion noises (such as abrupt mouse head jitters lasting less than two frames, or the small-amplitude vibration of the snout points due to non-uniform luminance conditions, etc.) using a 3-point medium filter. However, a variety of arrangements can be used as discussed above to implement the present OMR detection algorithm and similar protocols.

The present OMR detection algorithm performed OMR detection based on the mouse head orientations and snout trajectory in the latest 20 frames (equivalent to 0.67 second with the 30 fps camera). When a new image frame was captured, the mouse head was regarded to be in a tracking state and a positive OMR indicator was recorded if the following three conditions were simultaneously met: (1) the displacement of mouse snout between any two successive frames in the latest 20 frame time was below a threshold d (meaning no large motions); (2) the accumulated head rotation (measured as unwrapped head orientation difference between the first and the last of the latest 20 frames) exceeded an angular threshold a in the direction of rotating stripes; (3) the accumulated snout movement (measured as the distance between snout coordinates of the first and the last of the latest 20 frames) was over a small distant threshold c. In contrast, the mouse head was regarded as to be in a pausing state and a negative OMR indicator was recorded if the following two conditions were simultaneously met: (1) the displacement of mouse snout between any two successive frames in the latest 20 frame time was below d; (2) the accumulated snout movement was below c/2 (regardless of the accumulated head rotation). Those thresholds are configurable to match various mouse sizes. Once either a positive or negative OMR indicator was recorded, the OMR detection was suspended during the next 19 frames to avoid repeated detections (but mouse head orientation and the snout trajectory were still recorded). Consecutive recordings of negative OMR indicators (such as the negative indicators detected at the 20th, 40th and 60th frames) were merged into one to further remove repeated OMR absence detections, as pausing status usually lasted for a longer time. However, consecutive positive OMR indicators were not merged, as occasional long-time head tracking behaviors were strong evidence that the mouse could see the rotating stripes. Again, a variety of approaches can be taken based on the present OMR detection algorithm. The examples provided herein are for illustrative purposes.

In the presently-used system, the stripe patterns were manually changed. The stimuli were always on until the presence or absence of OMR was confirmed, and the stimuli parameters, such as contrast or spatial frequency, were then changed manually. However, as understood by one skilled in the art, a fully-automated OMR system can be implemented based on the details herein, including changing the stimuli automatically.

Since many mice would get agitated when they came to the testing platform for the first time, the mice were pre-trained by sitting them in the OMR system with rotating strips for ~10 minutes the day before the OMR test so the mice were adapted to the system. Such acclimatization is a common practice in behavior studies. To measure visual functions including CS and VA, we implemented the 1-up-1-down staircase protocol (FIG. 5) for our OMR detection algorithm. Michaelson contrast definition was used in this study, and CS is the reciprocal of the lowest contrast perceivable by mice. VA was reported as the highest spatial frequency perceivable (in cpd) with highest contrast available in the test. The smallest CS step was set as 0.063, and the smallest VA step as 0.050 cpd (~8% of the VA range from 0.06 to 0.72 cpd). Comparing to Snellen vision charts designed for human beings, which grade human VA by 11 levels from 20/200 to 20/10 with smallest step of 3 cpd (10% of the range), the VA step in our study was reasonably small.

The protocol was specified by two parameters: head movement count m and staircase reversal count s. If the count of positive OMR indicators (head tracking movements) reached m before the count of negative OMR indicators (head pausing status) reached 3 m, the protocol asserted an OMR presence (implying that the mouse was able to see the stimuli) and set the stimulus one level harder, i.e. lower contrast (for CS assessment) or higher spatial frequency (for VA assessment). When the count of negative indicators reached 3 m before the count of positive ones reached m, the protocol asserted an OMR absence (implying that the mouse failed to see the stimuli) and set the stimulus one level easier. The count of trial reversals between one OMR presence and one OMR absence must reach s before a conclusive final vision measurement.

The study included two stages. The first stage aimed to choose an optimal staircase protocol, and the second stage validates the application feasibility of the optimal protocol. We selected the optimal protocol from 12 possible candidates with different combinations of head movement count m (m=1, 2 or 3) and staircase reversal count s (s=1, 2, 3 or 4). Each protocol candidate was evaluated on three merits: CS, CS fluctuation, and time consumption for the measurement. The CS fluctuation for protocol (m, s) was defined as:

$$CS\_Fluctuation(m,s) = |CS(m,s) - CS(m,4)| \quad (1)$$

Here the measured CS was used with s=4 as a reference to compute the fluctuation, since empirically more reversals generate more converged and thus more accurate test results (unless the subject is too tired to continue the test).

All animal procedures were performed in accordance with the statement of the Association for Research in Vision and Ophthalmology, and the protocols were approved by Institutional Animal Care Committee (IACUC) of the Schepens Eye Research Institute. Mice were housed in a temperature-controlled room with a 12 h light/dark cycle. Fresh water and rodent diet were available at all times. Adult C57BL/6J wild-type (WT) and Balb/c mice were purchased from Jackson Laboratory, and mice deficient for Rhodopsin ($Rho^{-/-}$) were a gift from M. Young's Lab at Schepens that was originally developed by Humphries and his team, and were bred at the animal facility of the Schepens Eye Research Institute. Mouse genotype was verified by polymerase chain reaction (PCR) for tail DNA as previously described.

To select the optimal staircase protocol, comparison of the impact of choosing different m and s values on measured CS, CS fluctuation, and consumed test time were made, as mentioned above. SPSS (version 11.5) was used to analyze the two protocol parameters. The normality was first checked of the CS data for the 9 WT and 3 $Rho^{-/-}$ mice, grouped under each of the 12 different combinations of m and s values, and found the data were not significantly different from the normal distribution. Parametric methods, repeated measures ANOVA, and paired T-tests, were used in the statistical analyses. A p value smaller than 0.05 was regarded as statistical significance.

Thus, using both wild-type (WT) and Rhodopsin deficient ($Rho^{-/-}$) mice that exhibited progressive retinal degeneration, demonstration was made of the validity and efficiency of the present OMR detection algorithm. The $Rho^{-/-}$ mice are an art-recognized mouse model for the human condition. Use of an unbiased and rapid OMR assay for assessment of visual functions in mice, such as discussed herein, would greatly facilitate the drug discovery process and enable large-scale visual behavior phenotyping in animals. These uses can then be used to assist in development of effective treatments in humans.

Exemplary Test Data:

FIGS. 13A, 13B, 14A, and 14B additionally illustrate data collected when comparing the sensitivity of the present OMR detection algorithm to human-detected CS and VA data. The data and results discussed herein and illustrated in FIGS. 13A-B and 14A-B are for illustrative purposes only and should not be construed to limit applied methods or possible results in any way. The data specifically compared the OMR results obtained by the present OMR detection algorithm with that obtained from human observers on Rho$^{-/-}$ mice of a genetically modified mouse strain that carries Rhodopsin deficiency and exhibits progressive photoreceptor degeneration as discussed above.

The Rho$^{-/-}$ mice were placed on a pedestal that was placed in the center of an OMR system similar to that illustrated in FIG. 2 that contained an enclosure chamber formed by four 15-inch LCD monitors for displaying visual stimuli (herein black and white stripes). Visual functions of the Rho$^{-/-}$ mice were assayed starting from 6 weeks old before functional vision loss was detected. By varying bar width, and contrast, the thresholds of CS at a spatial frequency (0.20 cyc/deg) and VA of Rho-/- mice were determined by human observers and by the present OMR detection algorithm. Linear regression analysis was employed to assess the vision changes over time for both methods.

Figure 13:
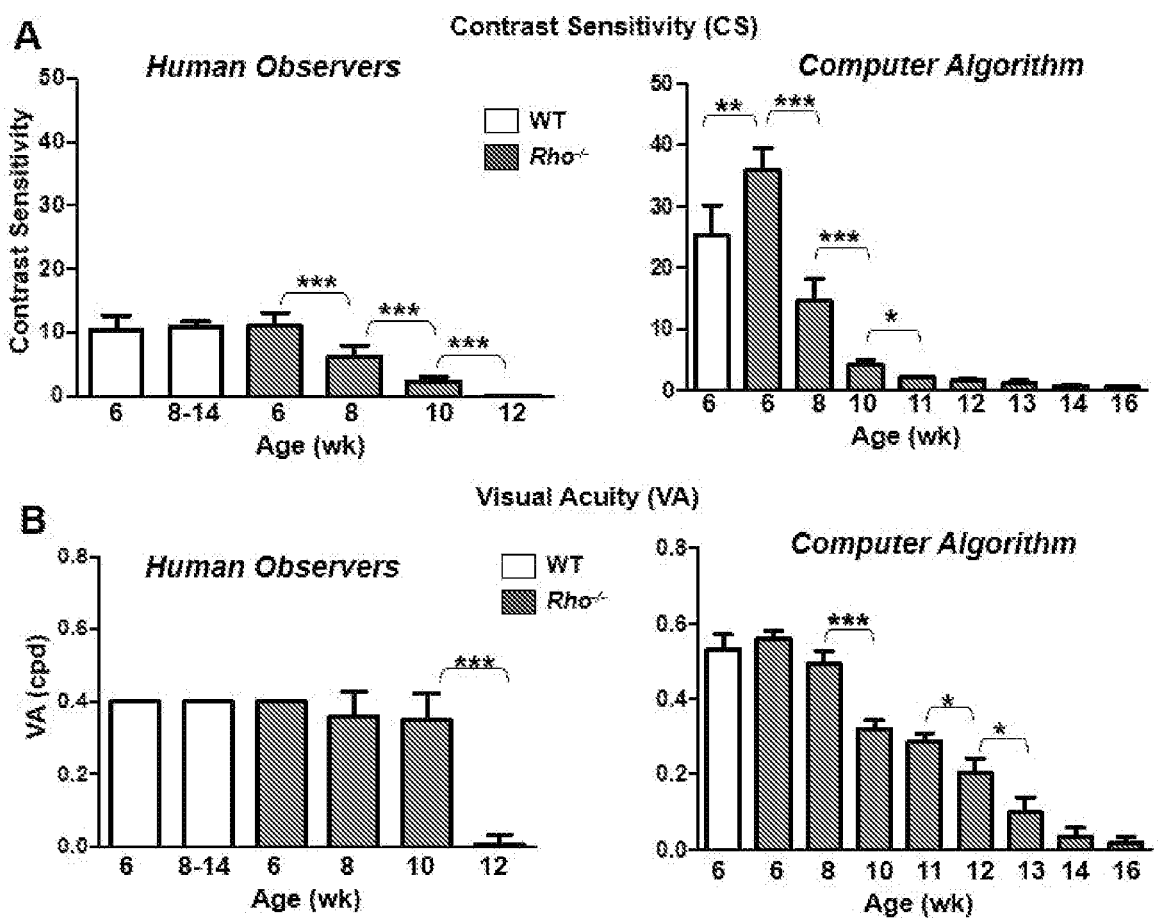
FIG. 13A illustrates an example analysis of results comparing the present OMR detection algorithm to human performance.
FIG. 13B illustrates an example analysis of results comparing the present OMR detection algorithm to human performance.

FIGS. 13A and 13B illustrate a significantly and surprisingly higher sensitivity of the present OMR detection algorithm (identified in the figure as the In-house Developed Computer Algorithm or Algo) when compared to human-detected CS and VA. For example, FIGS. 13A and 13B illustrate a comparison of CS and VA values of adult WT and Rho$^{-/-}$ mice assessed by human observers and the present OMR detection algorithm. FIG. 13A illustrates CS results, and FIG. 13B illustrates VA results of the adult WT (~6 weeks old; n=12) and Rho$^{-/-}$ mice of various ages (6-16 weeks old; n=11) detected by human observers (illustrated on the left side of the figures) and the present OMR detection algorithm (illustrated on the right side of the figures). The spatial frequency was set at 0.209 cpd for CS tests, and CS value was calculated by 1/Michelson Contrast with the Michelson Contrast equaling [(white bar luminance−black bar luminance)/(white bar luminance+black bar luminance)]. For data plotting, an arbitrarily assigned value of '0 VA' or '0.5 CS' was given to mice that were determined to be blind at the time examined (cpd=cycle per degree. *P<0.05; ***P<0.001. Value=mean±SEM).

FIGS. 14A and 14B illustrate a correlation of OMR and age of the Rho$^{-/-}$ mice. Specifically, FIGS. 14A and 14B illustrate correlative studies between CS and VA with mouse aging (progressive photoreceptor degeneration) in the Rho$^{-/-}$ mice. Linear correlations of CS, illustrated in FIG. 14A, and VA, illustrated in FIG. 14B, were assessed by human observers (illustrated on the left side of the figures) and the present OMR detection algorithm (illustrated on the right side of the figures) with the age of the Rho$^{-/-}$ mice. The R$^2$ value (representing a statistical measure of how close the data are to the fitted regression line) was also calculated. The present OMR detection algorithm detected better correlated and/or paralleled declines in CS and VA values along the age range in the Rho$^{-/-}$ mice than that detected by human observers. Thus, while both human observers and the present OMR detection algorithm can detect progressive vision loss in Rho-/- mice, the present OMR detection algorithm exhibits higher sensitivity and is capable of detecting smaller CS and VA gains in mice compared to human observers. The present OMR detection algorithm also provides higher lineated readings and requires much less time for each test (~3' vs 20' by humans). As such, the present OMR detection algorithm performs significantly better across every measurement considered. Additionally, as discussed above, the present OMR detection algorithm provides better results when compared to other approaches in the art that do not rely on human observers. As such, the present OMR detection algorithm provides better results generally, both when compared to human observers and when compared to more automated processes used currently in the art.

While specific results and specific algorithms, processes, and protocols are discussed herein, any algorithms, processes, and protocols can be used herein to analyze movement of a test subject and to assess visual functions of the test subject based on the movement.

While there have been shown and described illustrative embodiments that provide for assessment of visual functions, such as through OMR assay, it is to be understood that various other adaptations and modifications may be made within the spirit and scope of the embodiments herein. For instance, while a device is frequently mentioned throughout the present disclosure, the techniques described herein may also be implemented on various computers or similar machines. Thus, the embodiments of the present disclosure may be modified in any suitable manner in accordance with the scope of the present claims.

The foregoing description has been directed to embodiments of the present disclosure. It will be apparent, however, that other variations and modifications may be made to the described embodiments, with the attainment of some or all of their advantages. Accordingly, this description is to be taken only by way of example and not to otherwise limit the scope of the embodiments herein.

What is claimed is:

1. An assessment device for assessing visual functions of a test subject, comprising:
   at least one processor, memory, a visual stimulus unit, a platform, and at least one input device, wherein the assessment device is formed to create an enclosed area defined at least by the platform providing an area for the test subject to i) stand on the platform during a testing procedure and ii) move freely during the testing procedure;
   wherein the assessment device is configured to operate the testing procedure comprising:
      receiving the test subject in the enclosed area on the platform;
      displaying, using the visual stimulus unit, visual stimuli to the test subject on the platform in the enclosed area;
      tracking head movement of the test subject, i) using the at least one input device and ii) while the visual stimuli is being displayed to the test subject on the platform in the enclosed area configured to monitor movement of the test subject comprising tracking a plurality of points of a head of the test subject, a first point being associated with a first ear of the test subject, and a second point being associated with a second ear of the subject, and a third point being associated with a snout of the test subject; and
      determining a relationship between the head movement of the subject and the visual stimuli;
   and wherein the assessment device is configured to determine if a head pausing count reaches one or more times a variable value before a head tracking movements count reaches the variable value,
   wherein at which point the assessment device is configured to determine that the test subject cannot see the visual stimuli, and the processor is configured to set the visual stimuli at a higher contrast or at a lower spatial frequency.

2. The device of claim 1, wherein the visual stimulus unit includes at least one display unit.

3. The device of claim 1, wherein the input device includes at least one camera.

4. The device of claim 3, wherein the camera includes an infrared camera.

5. The device of claim 1, wherein the visual function includes acuity and contrast sensitivity.

6. The device of claim 1, wherein the visual function includes photoreceptor cone or rod mediated function.

7. The device of claim 1, wherein the visual stimuli include bars that change colors.

8. The device of claim 1, wherein the visual stimuli include changing a lumen of the visual stimulus unit.

9. The device of claim 1, wherein the visual stimuli include moving black and white bars at predefined widths and speeds and moving at a preset direction of either clockwise or counter-clockwise.

10. The device of claim 1, wherein the visual stimulus unit includes one or more LCD screens configured to display rotating stripes, and the LCD screens all display black and white bars at a same predefined width moving in one simultaneous direction.

11. The device of claim 1, wherein the processor is configured to assess contrast sensitivity and visual acuity by optomotor reflex protocol based on a head movement count and a staircase reversal count of the test subject.

12. The device of claim 11, wherein the head movement count includes head tracking movements of the test subject and head pausing of the test subject.

13. The device of claim 12, wherein head pausing of the test subject is configured to indicate that the test subject cannot see the visual stimuli.

14. The device of claim 11, wherein the processor is configured to determine if a head tracking movements count reaches a variable value before a head pausing count reaches one or more times the variable value, wherein at which point the processor is configured to determine that the test subject can see the visual stimuli, and the processor is configured to set the visual stimuli at a lower contrast or at a higher spatial frequency.

15. The device of claim 14, wherein the processor is configured to determine if the head tracking movements count reaches the variable value before a head pausing count reaches 3 times the variable value.

16. The device of claim 1, wherein the processor is configured to determine if the head pausing count reaches 3 times a variable value before a head tracking movements count reaches the variable value.

17. The device of claim 1, wherein the input device includes a camera.

18. The device of claim 17, wherein the camera includes an infrared camera.

19. The device of claim 1, wherein the processor is configured to determine an orientation of a head of the test subject based on a contour extraction of the test subject, a point of maximum curvature on the contour of the test subject, and a computation from the point of maximum curvature and two side points that have equal distance from the point of maximum curvature along the contour.

20. The device of claim 1, wherein the at least one input device is a camera positioned above the platform and oriented vertically such that the camera is capable of capturing images of the test subject in the enclosed area on the platform.

* * * * *